US006239137B1

(12) United States Patent
Karmali et al.

(10) Patent No.: US 6,239,137 B1
(45) Date of Patent: *May 29, 2001

(54) SALTS OF AMINOIMIDAZOLE CARBOXAMIDE AND 5 AMINO OR SUBSTITUTED AMINO 1,2,3-TRIAZOLE, INDUCE APOPTOSIS, INHIBIT DNA SYNTHESIS AND CONTROL CYCLOOXYGENASE ACTIVITY

(75) Inventors: Rashida A. Karmali, New York, NY (US); Felix Wehrmann, Vienna (AT)

(73) Assignee: Savvipharm INC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/231,147

(22) Filed: Jan. 15, 1999

Related U.S. Application Data

(63) Continuation-in-part of application No. 08/684,297, filed on Jul. 18, 1996, now Pat. No. 5,861,406, which is a continuation-in-part of application No. 08/505,439, filed on Jul. 21, 1995, now Pat. No. 5,728,707.

(51) Int. Cl.[7] .................. A61K 31/515; A61K 31/4164
(52) U.S. Cl. .................. 514/274; 424/85.4; 424/85.7; 512/2; 512/21; 512/359; 512/386
(58) Field of Search .................. 424/85.4, 85.7; 514/2, 21, 274, 359, 386; 544/310; 548/255, 326.5

(56) References Cited

U.S. PATENT DOCUMENTS

| | | | |
|---|---|---|---|
| 4,590,201 | 5/1986 | Bochis et al. | 514/359 |
| 5,045,543 | 9/1991 | Hupe | 514/359 |
| 5,132,315 | 7/1992 | Kohn et al. | 514/359 |
| 5,728,707 | * 3/1998 | Wehrman | 514/274 |
| 5,861,406 | * 1/1999 | Wehrman | 514/274 |

OTHER PUBLICATIONS

Thompson CB, 1995, Science 267:1456–1462.
Raff MC, 1992, Nature Lond. 356:397–400.
Felder et al. 1991, J. Pharmacol. Exp. Thr. 247:967–971.
Scahs L et al. 1993, Blood 82:15–21.
Hockenberg DM et al., 1993, Cell 75:241–251.
Wang HG et al. 1996, Proc. Natl. Acad. Sci. USA 93:7063.
Karmali RA et al. 1982, Prost. Lenk. Med. 8–437–446.
Karmali RA 1987, Eur. J. Chin. Oncol. 23:3–7.
DeWitt DL, Biochim. Biophys. Acta 1991, 1083:121–134.
Ken JRF et al., 1994, Cancer B:2013.
Santen RJ, 1992, J. Chim. Endocrinol. Metab. 75:685–689.
Isaacs J et al., 1992, J. Androl. 13:457–464.

* cited by examiner

Primary Examiner—Richard L. Raymond

(57) ABSTRACT

Compositions and methods are described for the induction of apoptosis inhibition of DNA synthesis, and/or inhibiting COX-2 activity using an effective amount of salts of aminoimidazole carboxamide, 5 amino 1,2,3-triazoles or a combination of salts thereof.

51 Claims, 18 Drawing Sheets

US 6,239,137 B1

Figure 1:
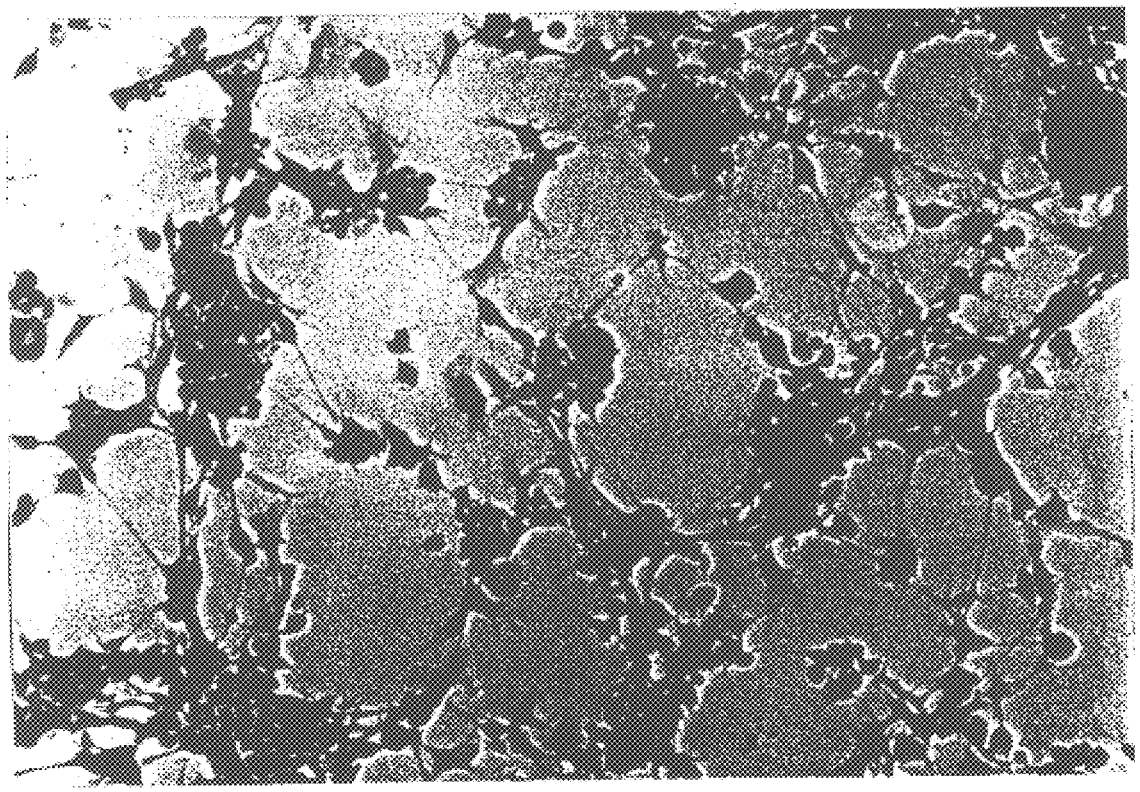

SALTS OF AMINOIMIDAZOLE CARBOXAMIDE AND 5 AMINO OR SUBSTITUTED AMINO 1,2,3-TRIAZOLE, INDUCE APOPTOSIS, INHIBIT DNA SYNTHESIS AND CONTROL CYCLOOXYGENASE ACTIVITY

CROSS-REFERENCE TO RELATED APPLICATIONS

This application is a continuation-in-part of U.S. application Ser. No. 08/684,297, filed on Jul. 18, 1996, now U.S. Pat. No. 5,861,406 which is a continuation-in-part of U.S. application Ser. No. 08/505,439, filed Jul. 21, 1995, now U.S. Pat. No. 5,728,707. The contents of these applications are incorporated herein by reference.

1. BACKGROUND OF THE INVENTION

The invention relates generally to compositions and methods that are effective in inducing apoptotic cell death and inhibiting replication and repair in normal, abnormal or cancerous cells.

Apoptosis or programmed cell death, is an essential physiological process required for development, homeostasis and protection by the immune system (Thompson, C. B., 1995, Science 267: 1456–1462). It is a property of animal cells, allowing unwanted cells to be eliminated quickly and neatly. Although the death program is cell-intrinsic, it is regulated by extracellular signals that can either activate it or suppress it (Raff, M. C., 1992, Nature London 356: 397–400). The dependence on survival signals ensures that a cell only survives when and where it is needed, just as dependence on growth factors for proliferation ensures that a cell only divides when a new cell is needed. The importance of such controls in multicellular organisms is illustrated by the devastating effects of proliferative diseases, inflammatory diseases, arteriosclerosis or cancer, where the controls are defective. Furthermore, attenuation of apoptotic potential is associated with cancer progression and resistance to chemotherapy. Some chemotherapeutics and other relevant cancer, anti-proliferative and anti-inflammatory therapies induce apoptosis in their targets and apoptosis resistance contributes to metastasis of some cancers such as prostate cancer (McConkey, D. J. et al., 1996, Cancer Res. 56:5594–5595). Therefore, agents that are effective inducers of apoptosis are needed to implement effective apoptosis and therefore, effective prevention and progression of proliferative diseases, cancer, arteriosclerosis and inflammatory diseases. Cytoplasmic shrinkage, chromatin condensation, and fragmentation of DNA are widely accepted distinguishing features of apoptotic cells. In contrast, necrotic cells typically display cytoplasmic swelling and lysis of the cell membrane and do not exhibit the condensed and fragmented chromatin associated with apoptosis.

The present invention demonstrates agents which induce apoptosis as well as modulate the activity of proliferating cell nuclear antigen (PCNA) which results in inhibition of replicative DNA synthesis. Eukaryotes contain six DNA polymerases including DNA polymerases $\epsilon$ and $\delta$ which are essential for replicative DNA synthesis. PCNA was identified as a specific auxiliary factor of polymerase $\delta$ and to stimulate polymerase $\epsilon$, implying that PCNA interacts with both polymerases and modulates replicative DNA synthesis (Tan, C. K. et al., 1986, J. Biol. Chem 261: 12310–12326; and Yoder, B. L. et al., 1991, J. Biol. Chem 266: 22689–22697). Therefore, agents that modulate PCNA activity which results in inhibition of replicative DNA synthesis are generally effective in inhibiting proliferative diseases, cancer cell development and proliferation, arteriosclerosis and inflammatory diseases.

The present invention is directed to compositions and methods using organic acid and inorganic acid salts of 5-amino-imidazole carboxamide (AICA) and/or of 5-amino or substituted amino, 1,2,3-triazoles (triazoles). For example, AICA and/or triazoles may be reacted with: a) aliphatic acids including, but not limited to, lactic, succinic, maleic, citric, tartaric or orotic; b) sugar acids including, but not limited to, gluconic or galactonic; or c) inorganic acids including, but not limited to, hydrochloric acid and phosphoric acid, to form salts suitable for use according to the compositions and methods of the present invention.

AICA salts have been used as hepatoprotectants based on their ability to prevent necrosis and stimulate regeneration of liver parenchymal cells. AICA orotate was also found useful in the inhibition of experimental prostatic cancer in rats (Cohen, L., Wehrmann, F. and Karmali, R. Proc. Am. Assoc. Cancer Res. 38:607).

Triazoles were originally disclosed as having anticoccidial activity in poultry (U.S. Pat. No. 4,590,201, issued May 20, 1986), and later in the treatment of peritoneal carcinomatosis of ovarian cancer (U.S. Pat. No. 4,132,315, issued Jul. 21, 1992 and Kohn, E. C et al., 1990, J. Natl. Cancer Inst. 82: 54–60), and of the PMT-6 fibrosarcoma tumor model in mice (U.S. Pat. No. 5,045,543, issued Sep. 3, 1991). One triazole compound in particular, the 5-amino-1-(4-[4-chlorobenzoyl]-3,5-dichlorobenzyl-1,2,3-triazole-4-carboxamide, designated L651582 (Merck Research laboratories, U.S. Pat. No. 4,590,201) was shown to inhibit cell proliferation, inflammation and some signal transduction pathways including those which involve calcium influx, the release of arachidonic and the generation of inositol phosphates (Kohn, E. C. et al., 1992, Cancer Res. 52: 3208–3212; and Felder et al., 1991, J. Pharmacol. Exp. Ther. 257: 967–971). Furthermore, the orotate salt of L651582 was shown to have a greater inhibitory effect on prostatic tumors in rats (Cohen, L., Wehrmann, F. and Karmali, R. Proc. Am. Assoc. Cancer Res. 38:607).

2. SUMMARY OF INVENTION

In accordance with the invention, compositions and methods are provided for inducing apoptosis, preventing development of and treating diseases by use of an effective amount of an AICA salt.

The present invention can also provide compositions and methods for induction of apoptosis, the prevention of disease development and treatment of diseases by use of an effective amount of a triazole salt. The preventive and/or treatment method involve inducing apoptosis, inhibiting replicative DNA synthesis, and/or inhibiting COX-2 activity to thereby prevent and/or treat a variety of diseases or conditions and provide a variety of benefits.

The present invention can also provide compositions and methods for induction of apoptosis, the prevention of disease development and treatment of diseases by use of an effective amount of an AICA salt and an effective amount of a triazole salt. The preventive and/or treatment method can involve inducing apoptosis, and/or inhibiting replicative DNA synthesis, inhibiting COX-2 activity to thereby prevent and/or treat a variety of diseases or conditions and provide a variety of benefits.

The present invention can also provide compositions and methods for induction of apoptosis, the prevention of disease development and treatment of diseases by use of an effective amount of an AICA salt and/or a triazole salt along with antioxidant therapy, including the administration of an effective amount of an antioxidant such as vitamin E, N-acetylcysteine, glutathione, vitamin C, cysteine, methionine, vitamin A and its analogues and/or 2-mercaptoethanol. The preventive and/or treatment method can involve inducing apoptosis, inhibiting replicative DNA synthesis, and/or inhibiting COX-2 activity to thereby prevent and/or treat a variety of diseases or conditions and provide a variety of benefits.

According to yet another aspect of the present invention, there is provided a method to induce apoptosis, and/or inhibit replicative DNA synthesis, inhibiting COX-2 activity in precancerous cells, aging cells, cancerous cells, preinflammatory cells, inflammatory cells or arteriosclerotic cells including the use of an AICA salt, and/or a triazole salt in combination with a conventional therapeutic regimen including radiation therapy, hormonal therapy or one or more cytotoxic agents.

The present invention also provides methods to induce apoptosis, and/or inhibit replicative DNA in precancerous cells, aging cells, cancerous cells, preinflammatory cells, inflammatory cells or arteriosclerotic cells, inhibiting COX-2 activity including the use of an AICA salt and/or a triazole salt in combination with an effective amount of n-3 fatty acids, alpha-linolenic, eicosapentaenoic and docosahexaenoic.

The present invention can provide a method of inducing apoptosis and/or inhibit replicative DNA synthesis in aging cells or in cells undergoing abnormal proliferation and/or inflammatory reactions, by applying an AICA salt and/or a triazole salt alone or in combination with an effective amount of one or more antioxidants including vitamin E, N-acetylcysteine, reduced glutathione, vitamin C, cysteine, vitamin A and its analogues, methionine or 2-mercapoethanol.

The present invention is based on the unexpected discovery that AICA salts and/or triazole salts are effective in inducing apoptosis, inhibiting replicative DNA synthesis, and/or inhibiting COX-2 activity.

It is the object of the present invention to provide a method for inducing apoptosis, inhibiting replicative DNA synthesis and/or inhibiting COX-2 activity in aging cells and/or tissues that show functional deficit and to trigger the renewal of cells and tissues.

It is also the object of the present invention to provide a method for inducing apoptosis, inhibiting replicative DNA synthesis, and/or inhibiting COX-2 activity in precancerous and cancerous cells.

It is also an object of the present invention to provide a method for inducing apoptosis, inhibiting COX-2 activity in cells undergoing abnormal proliferation and/or inflammation using an AICA salt and/or a triazole salt alone or in combination with each other and/or with an effective amount of one or more antioxidants.

Still other objects and advantages of the invention will in part be obvious and will in part be apparent from the specification.

3. BRIEF DESCRIPTION OF THE DRAWINGS

For a fuller understanding of the invention, reference is had to the following description taken in connection with the accompanying figures, in which:

FIG. 1 demonstrates PCNA staining in AT-1 prostate cancer cells treated with L651582.

Figure 2:
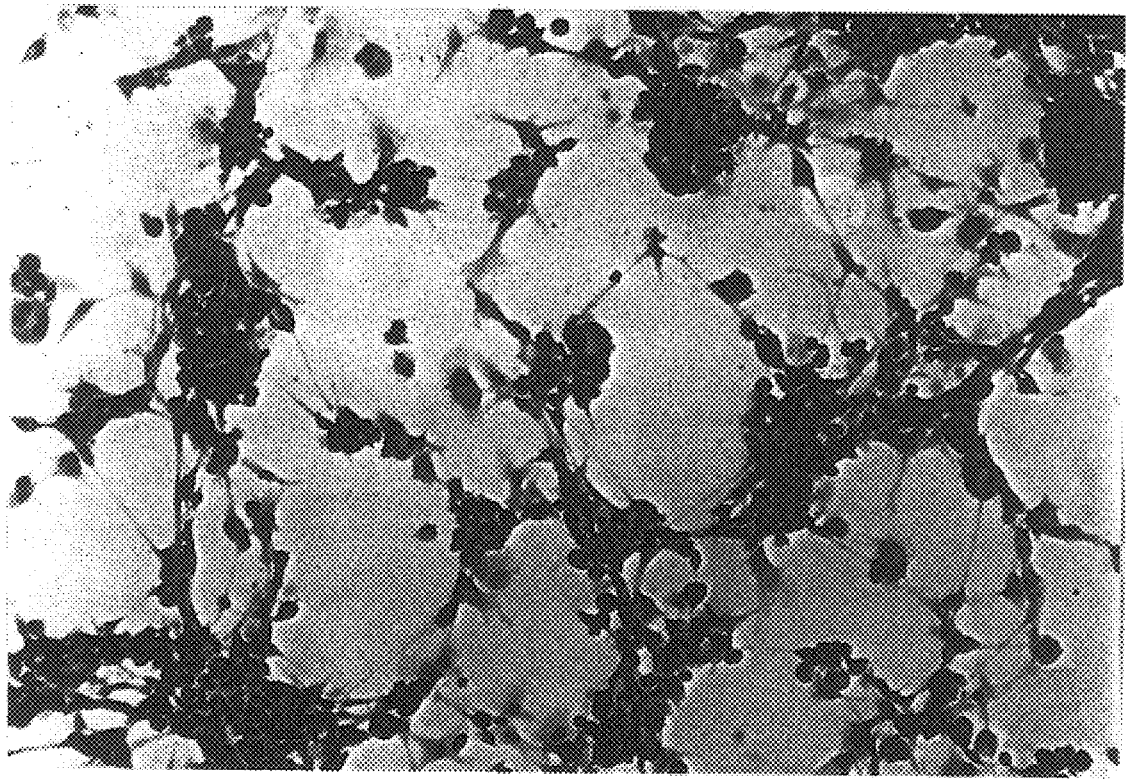

FIG. 2 demonstrates PCNA staining in AT-1 prostate cancer cells treated with L651582 orotate.

Figure 3:
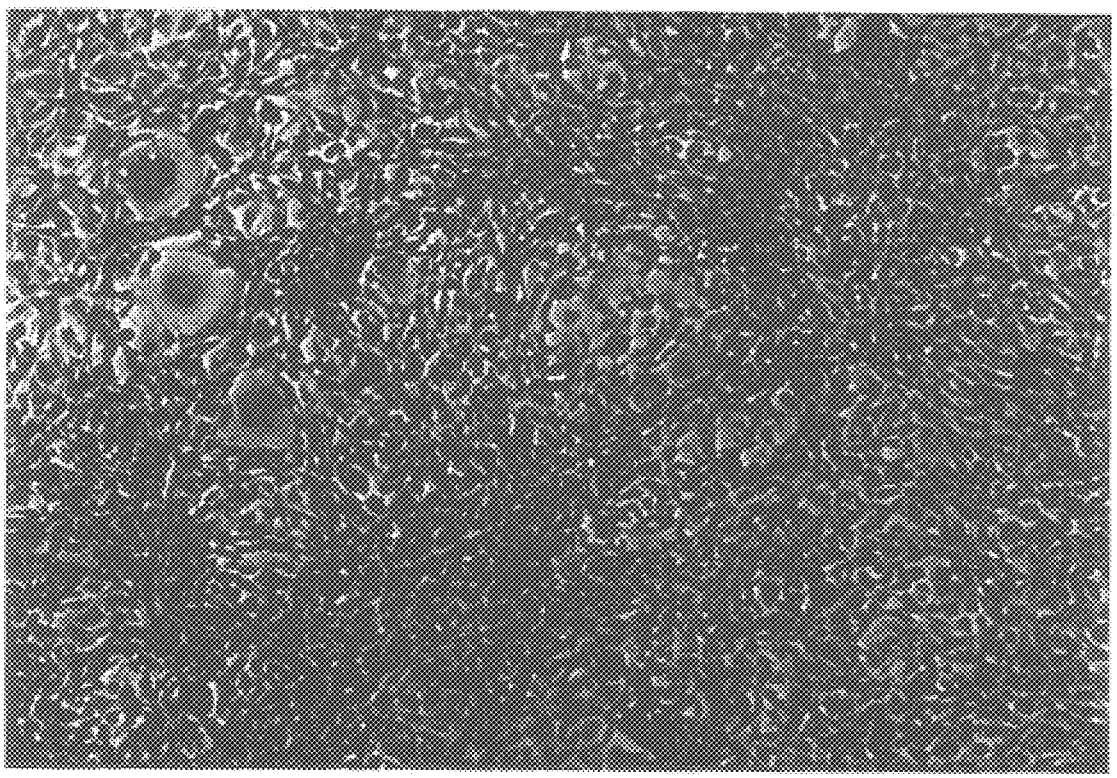

FIG. 3 demonstrates PCNA staining in AT-1 prostate cancer cells treated with control vehicle.

Figure 4:
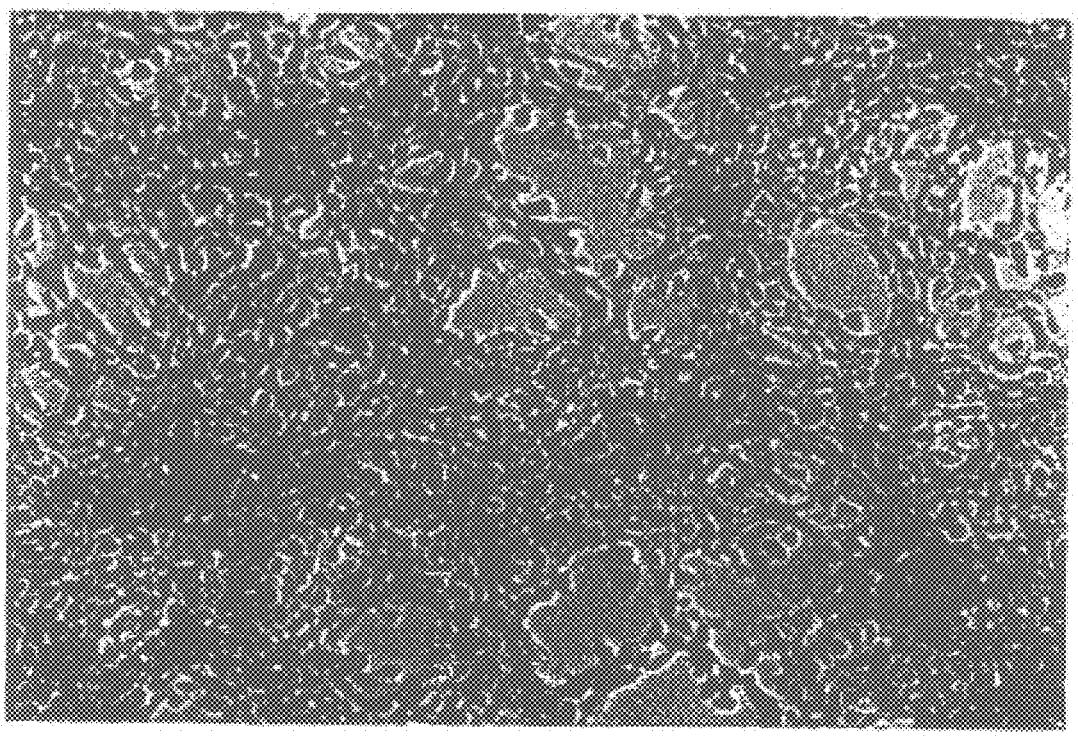

FIG. 4 demonstrates Klenow staining in MNU cells treated with L651582.

Figure 5:
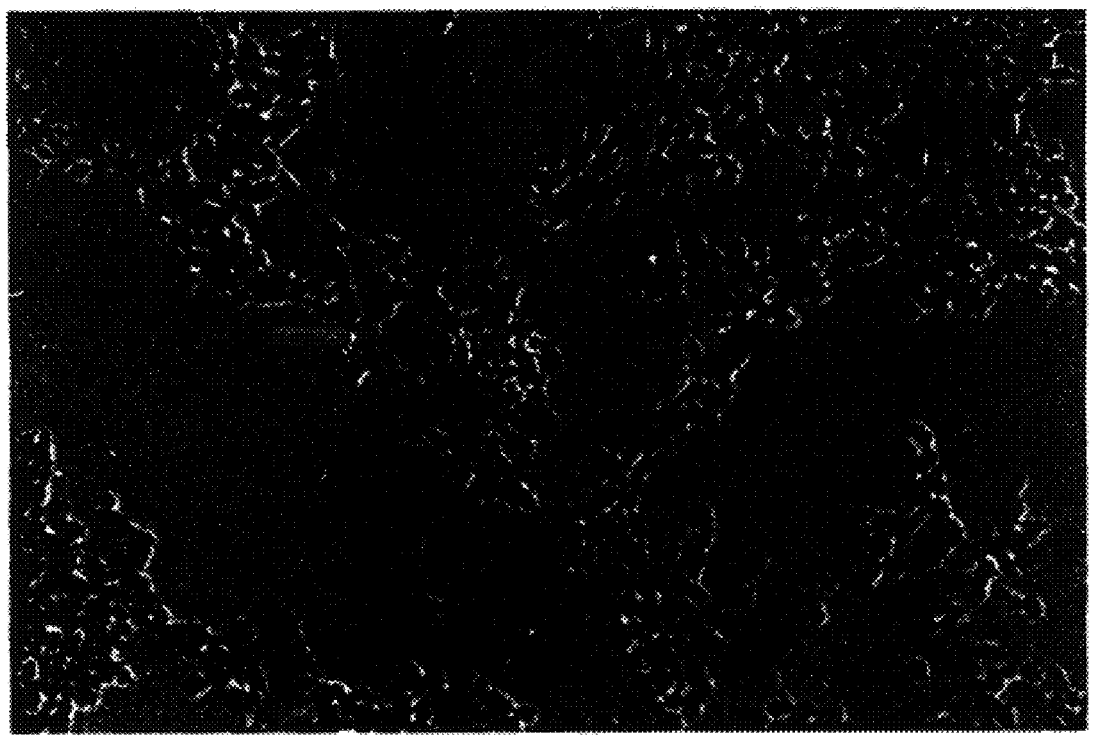

FIG. 5 demonstrates Klenow staining in MNU cells treated with L651582 orotate.

Figure 6:
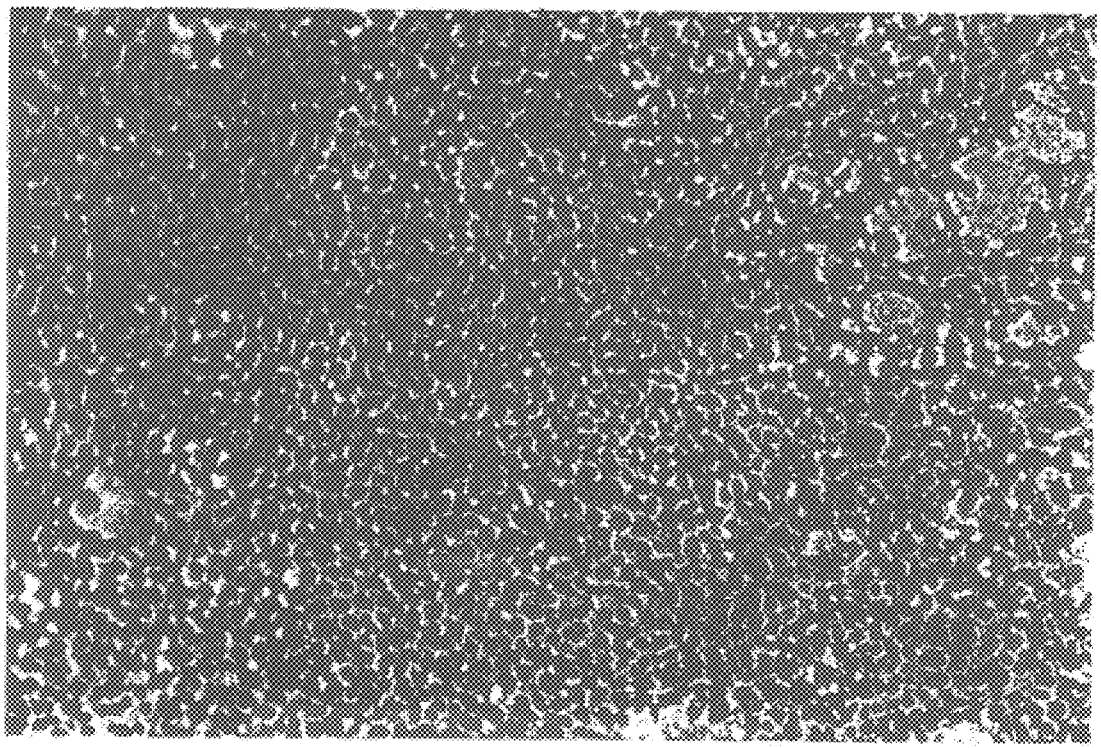

FIG. 6. demonstrates Klenow staining in MNU cells treated with control vehicle.

Figure 7:
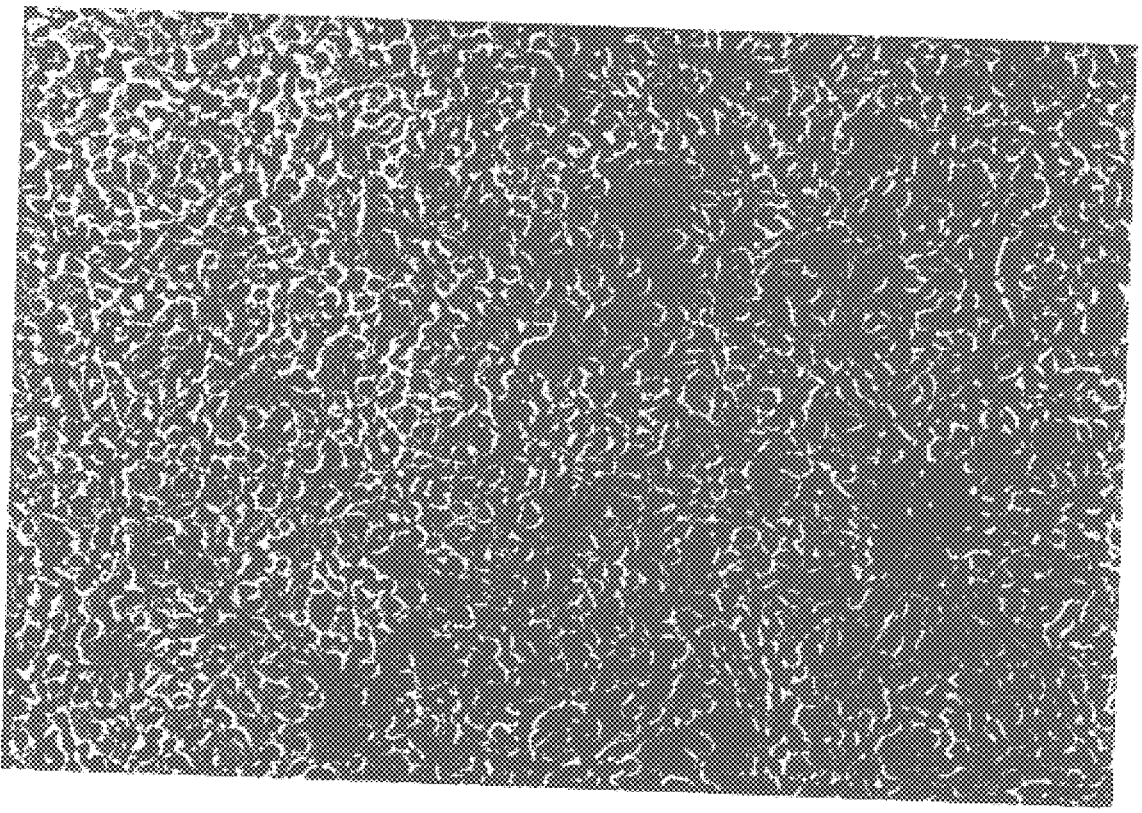

FIG. 7 demonstrates Klenow staining in AT-1 prostate cancer cells treated with orazamide orotate.

Figure 8:
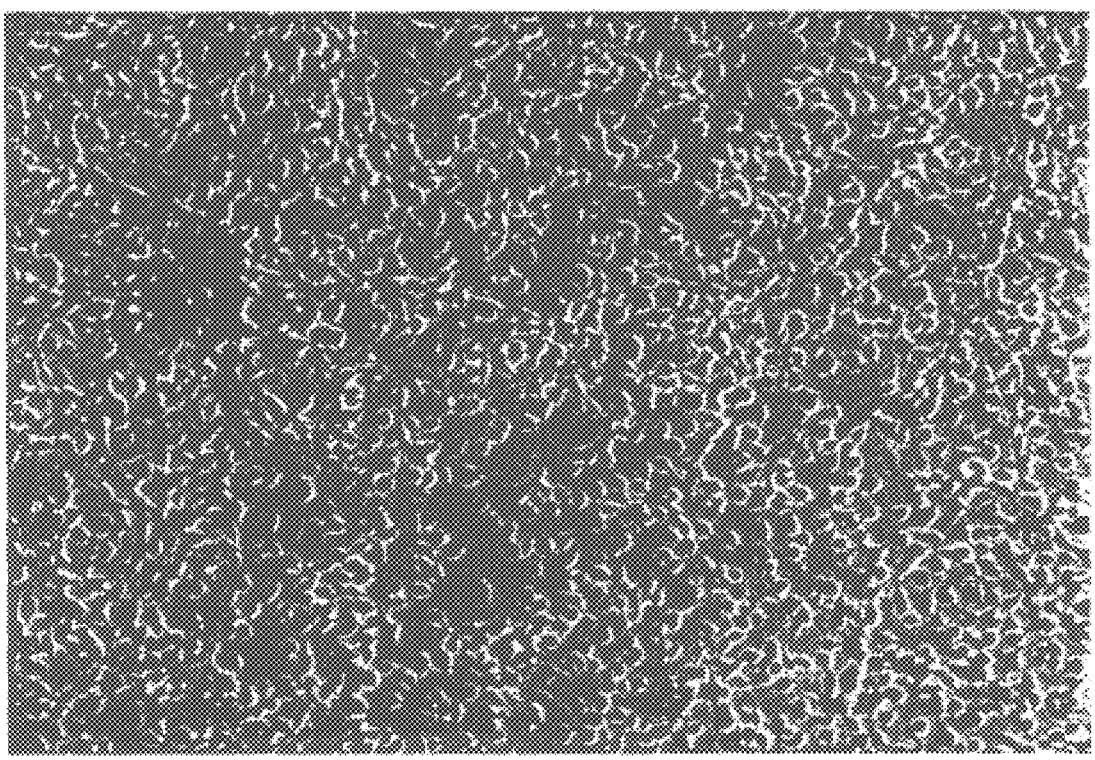

FIG. 8 demonstrates Klenow staining in AT-1 prostate cancer cells treated with Orazamide HCL.

Figure 9:
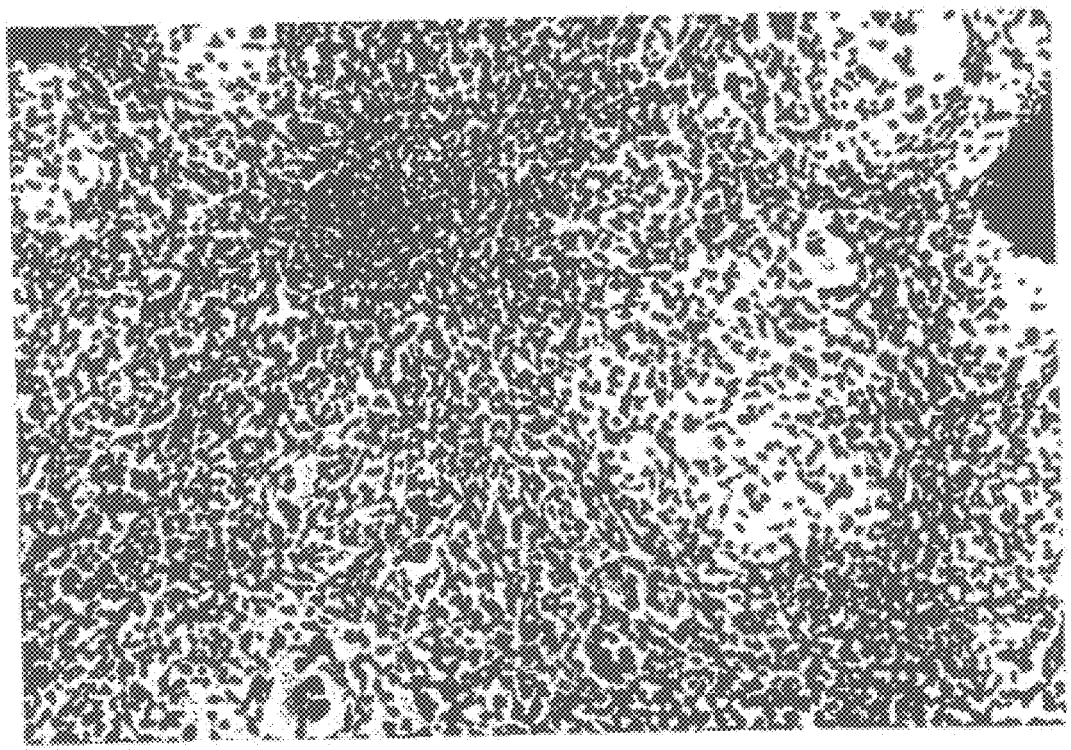

FIG. 9 demonstrates Klenow staining in AT-1 prostate cancer cells treated with L651582.

Figure 10:
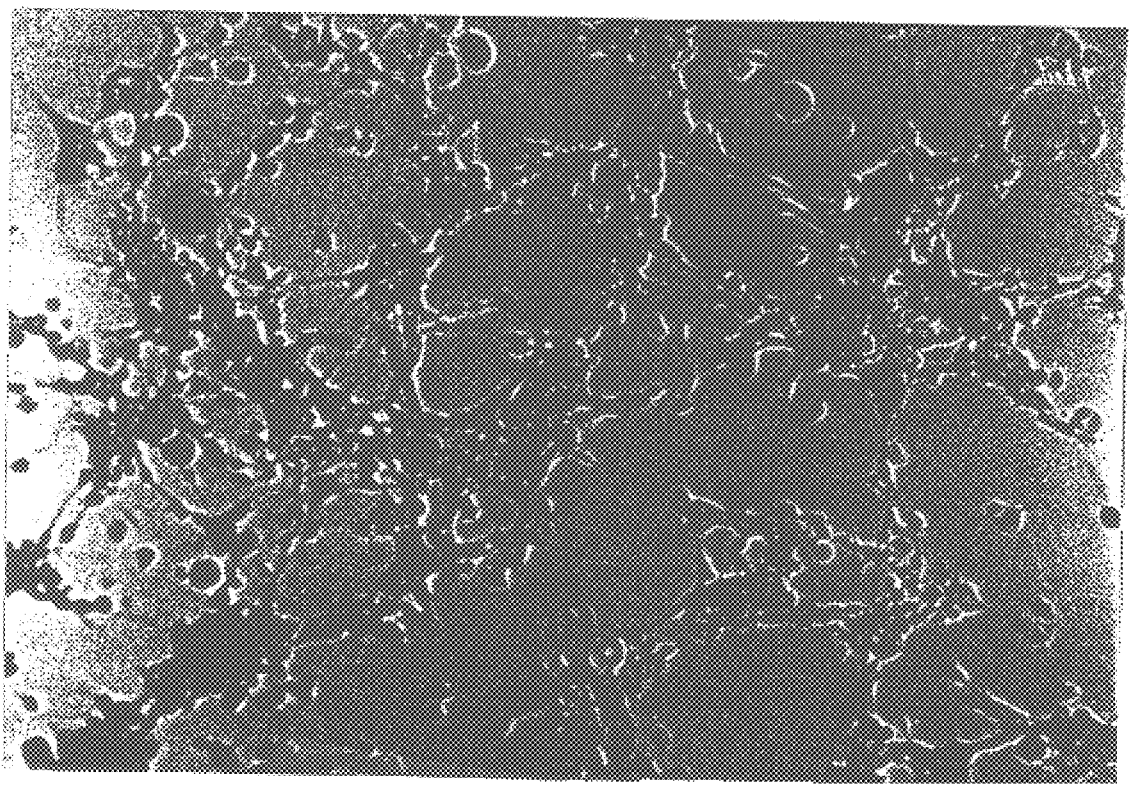

FIG. 10 demonstrates Klenow staining in AT-1 prostate cancer cells treated with L651582 orotate.

Figure 11:
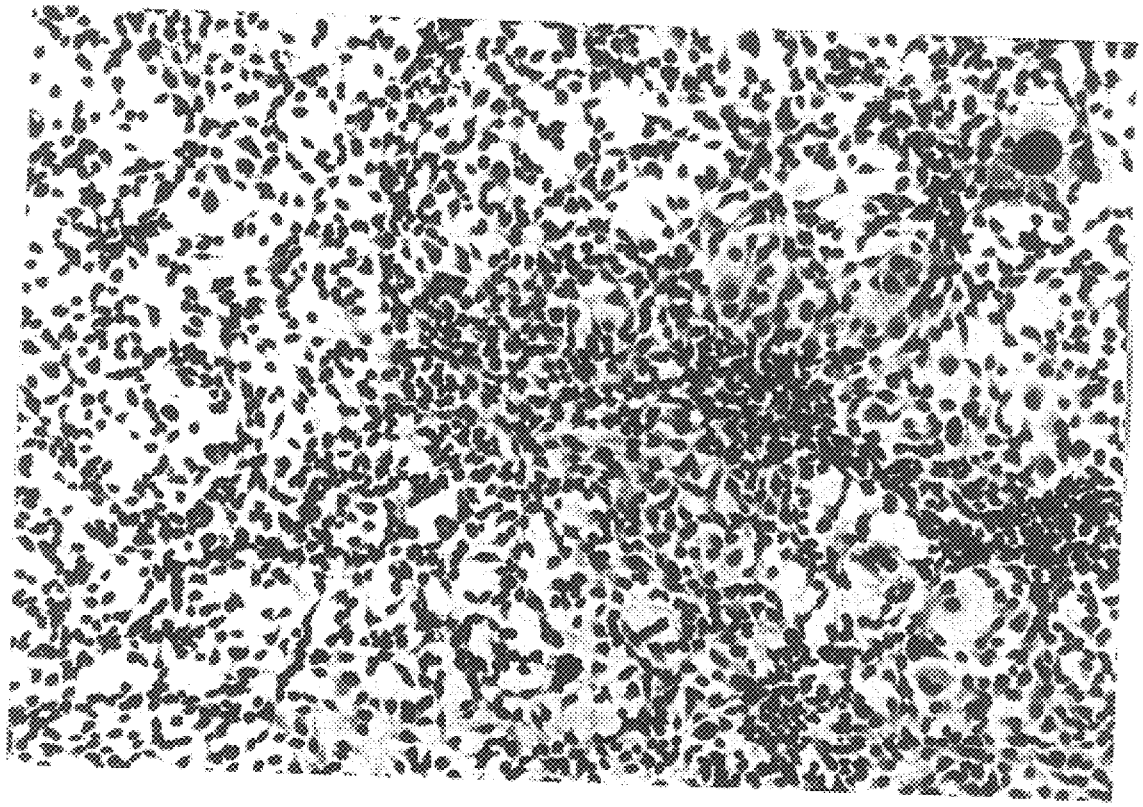

FIG. 11 demonstrates Klenow staining in AT-1 prostate cancer cells treated control vehicle.

Figure 12:
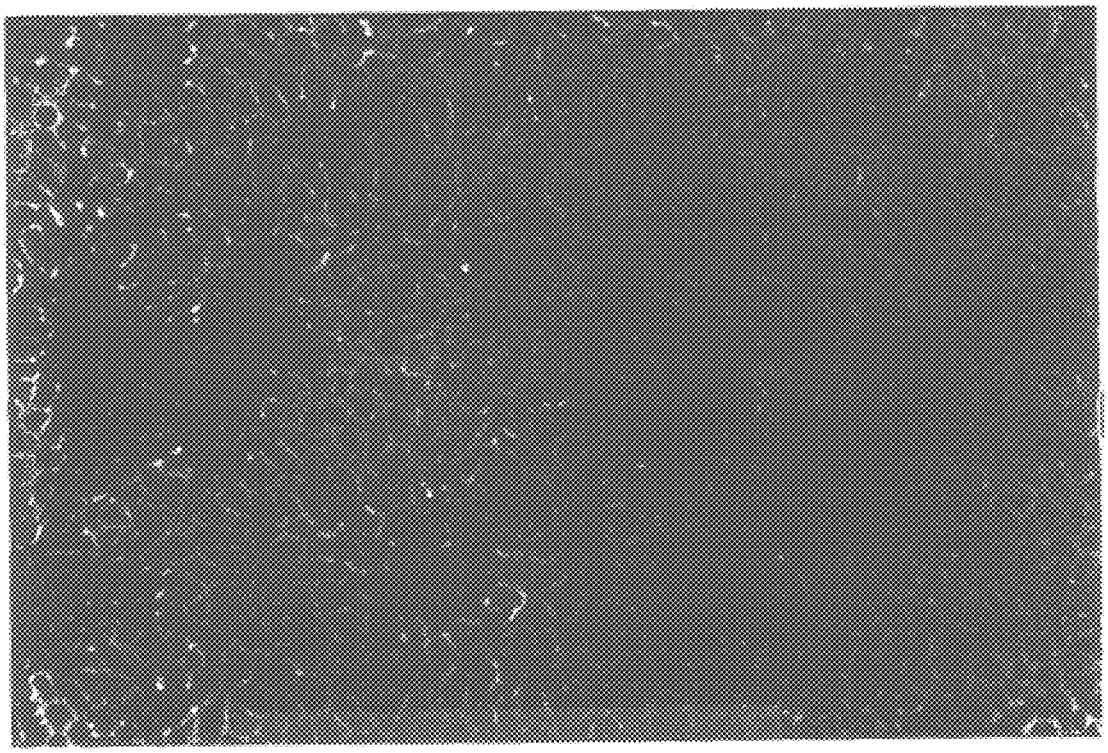

FIG. 12 demonstrates bcl2 staining in MNU cells treated with orazamide orotate.

Figure 13:
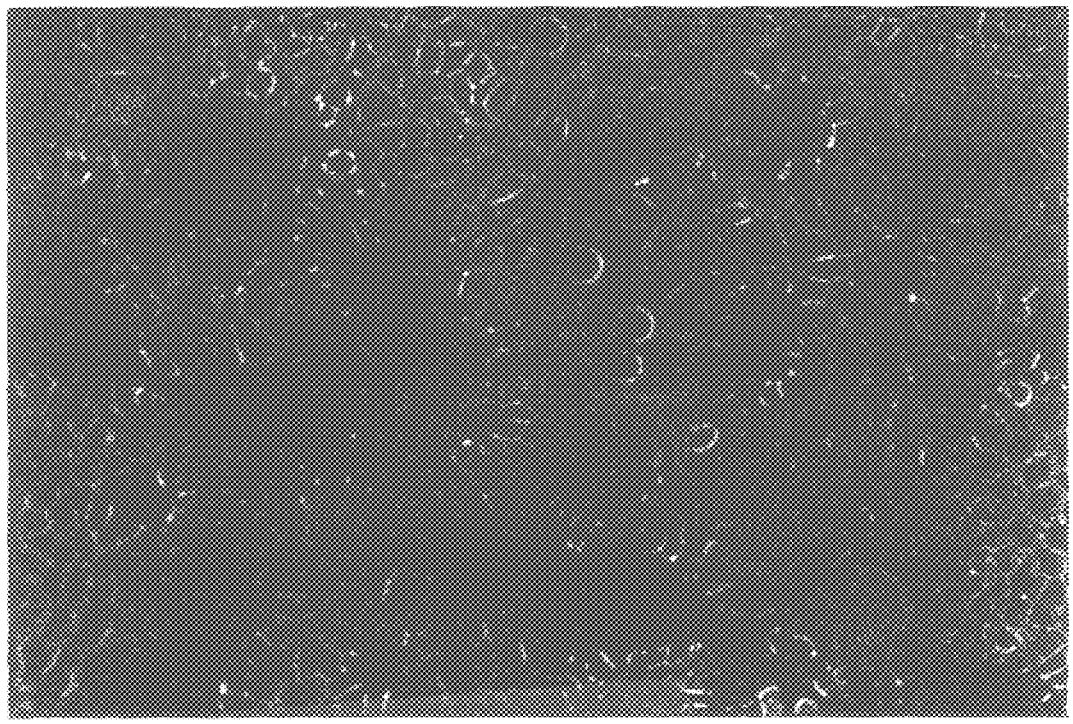

FIG. 13 demonstrates bcl2 staining in MNU cells treated with orazamide HCL.

Figure 14:
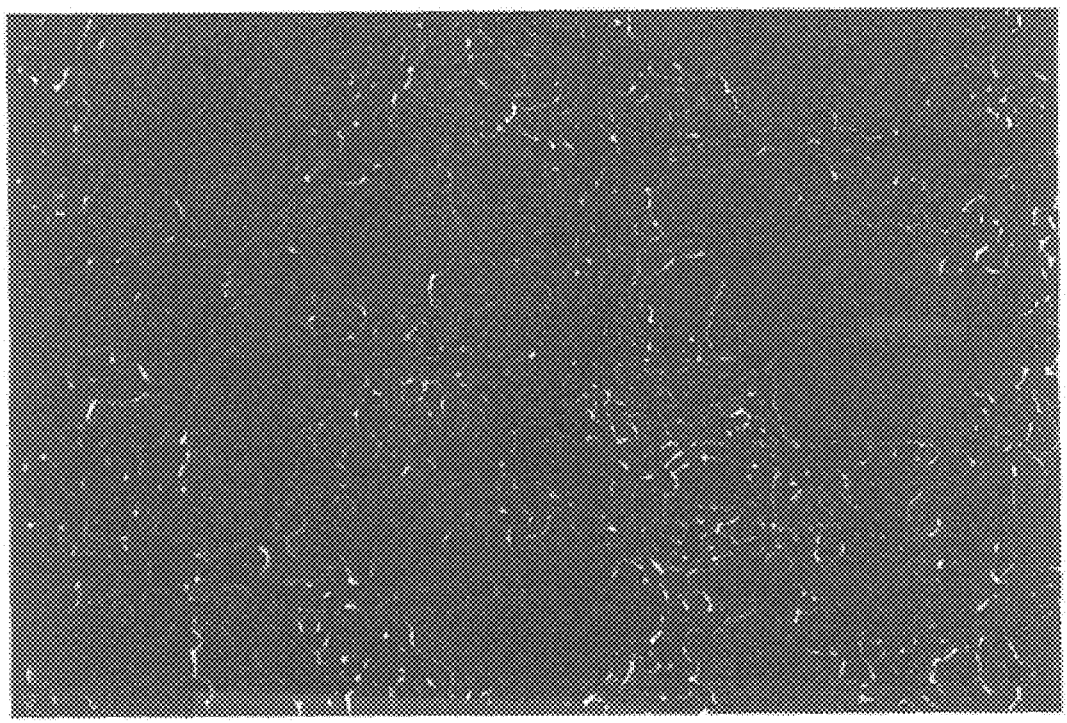

FIG. 14 demonstrates bcl2 staining in MNU cells treated with L651582.

Figure 15:
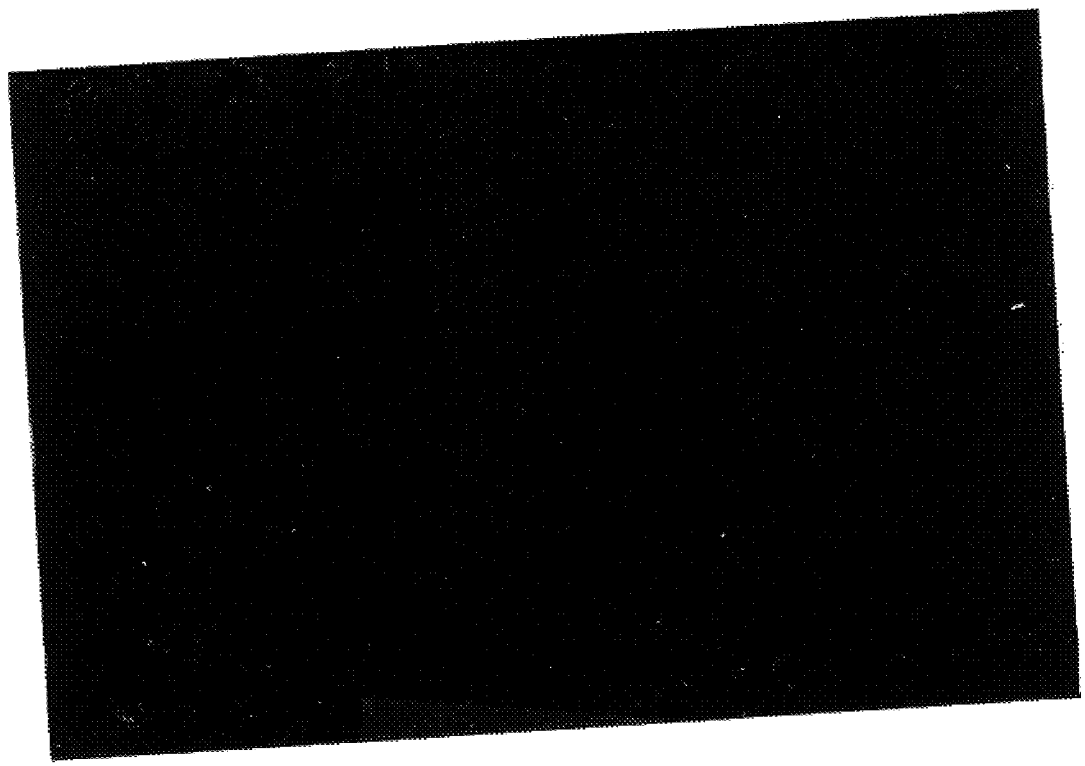

FIG. 15 demonstrates bcl2 staining in MNU cells treated with L651582 orotate.

Figure 16:
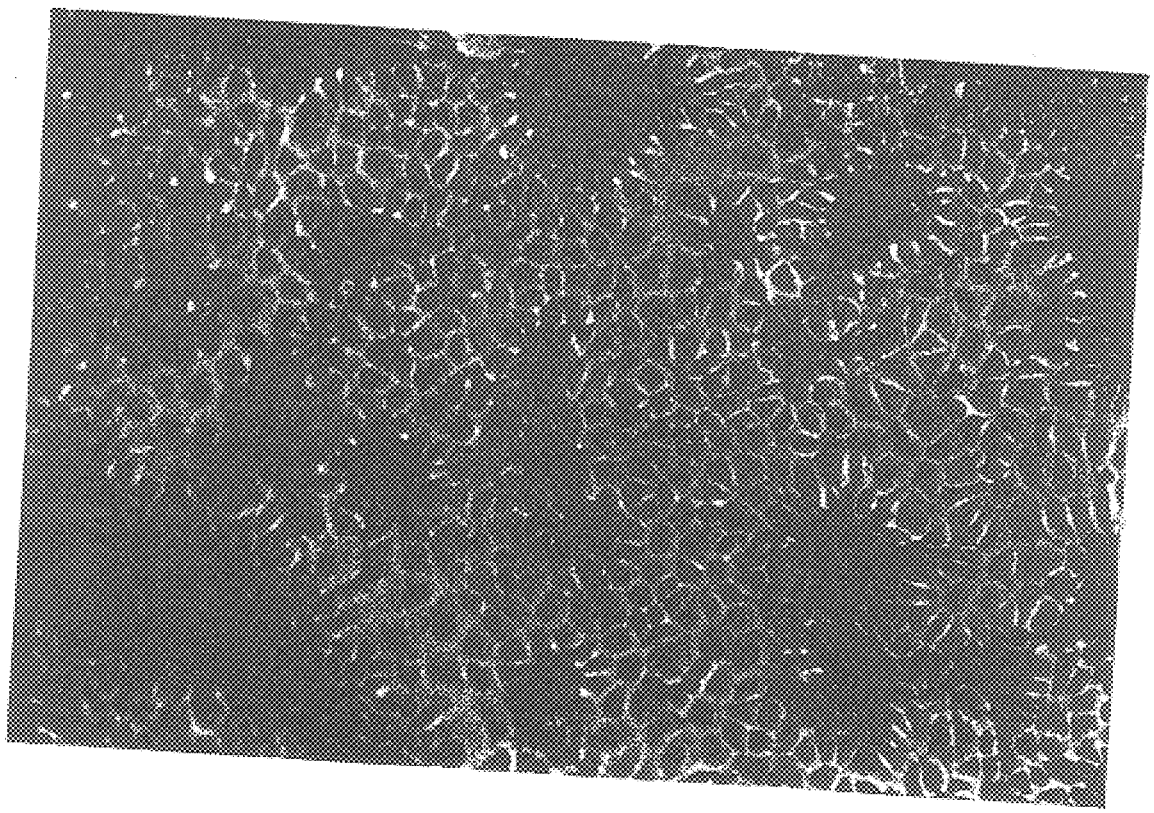

FIG. 16 demonstrates bcl2 staining in MNU cells treated with control vehicle.

Figure 17:
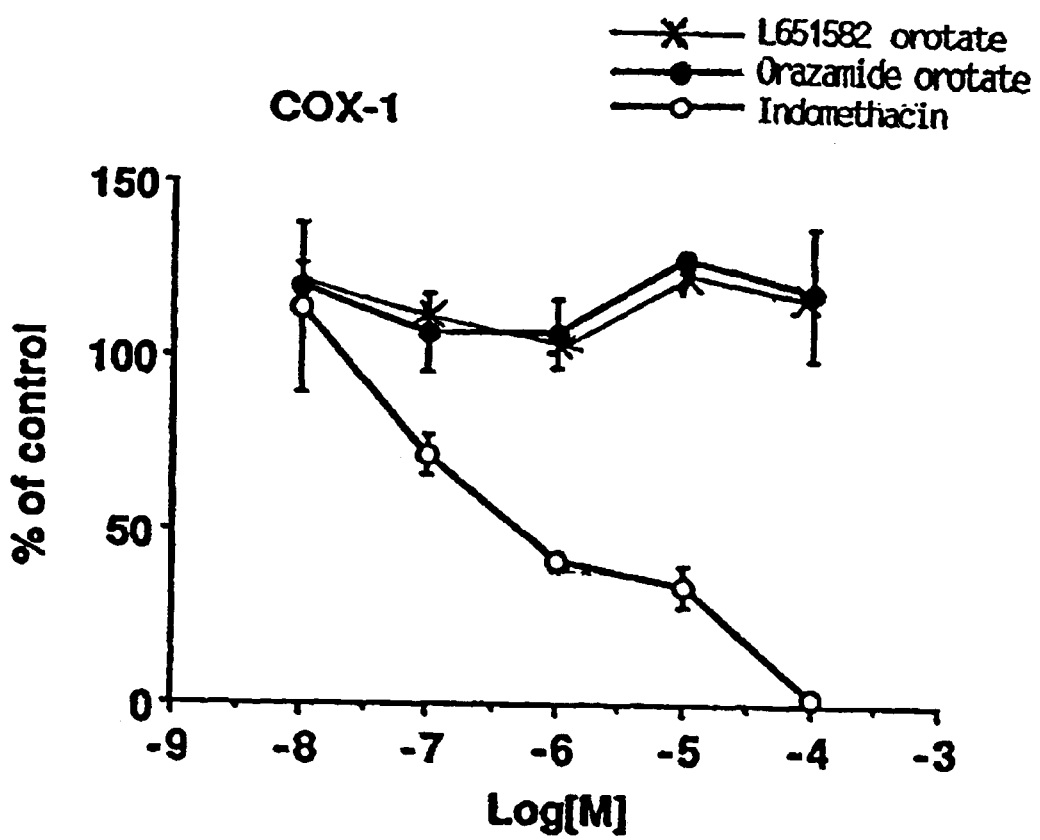

FIG. 17 demonstrates COX-1 activity expressed as % of control in response to orazamide orotate, L651582 orotate or indomethacin.

Figure 18:
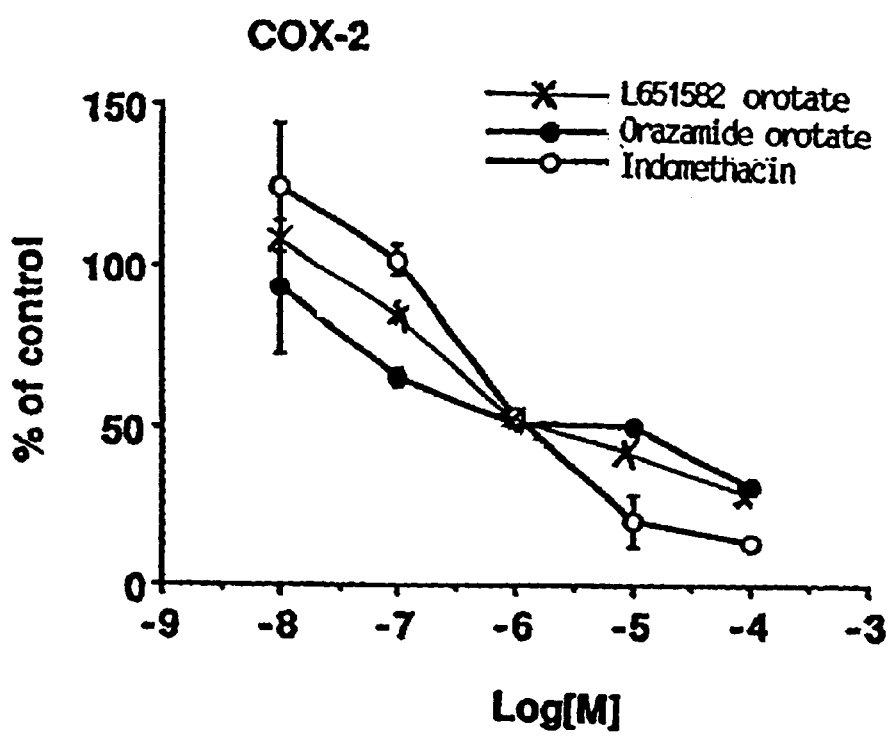

FIG. 18 demonstrates COX-2 activity expressed as % of control in response to orazamide orotate, L651582 orotate or indomethacin.

4. DETAILED DESCRIPTION OF THE INVENTION

The present invention generally pertains to compositions and methods for inducing apoptosis, inhibiting replicative DNA and/or in inhibiting COX-2 activity synthesis in treated cells. The disease prevention and application methods of the invention are fundamentally based on a newly discovered effect of AICA salts and triazole inducing apoptosis, PCNA activity and/or in inhibiting COX-2 activity in cells in vivo and in vitro.

The present invention can also provide a method for inducing apoptosis in aging cells and/or in tissues that show functional deficit to trigger their renewal.

The method of the invention involves administering an effective dose of an organic acid salt or inorganic acid salt of AICA or of 5-amino or a substituted amino 1,2,3-triazole, to an individual who is identified as being at enhanced risk for a proliferative disease, cancer, inflammatory diseases and/or arteriosclerosis.

It will be apparent to those skilled in the art that the other salts of AICA or triazole-related compounds which induce apoptosis, inhibit replicative DNA synthesis, and/or inhibit COX-2 activity may be useful.

It may be that the ability of AICA or triazole salts also to induce immunostimulation, to inhibit immunosuppression induced by chemotherapeutic agents and oxygen free radicals, contributes to their efficacy or effectiveness. These possible mechanisms of action are in no way meant to limit the scope of the invention and are presented purely for explanatory and/or illustrative purposes.

4.1 Apoptosis

Apoptosis is a general property of most cells and is necessary to achieve an adequate balance between the sufficient survival of cells and their overwhelming proliferation and expansion. This is of particular importance to prevent the formation of abnormal or malignant growth, but it is also necessary to limit expansion of immune cells challenged by pathogens or other stimuli, and as a defense mechanism to remove self-reactive lymphocytes. In aging cells and/or tissues that show functional deficit, apoptosis is a useful approach to increase the turnover of senescent cells and trigger the renewal of cellular function and structure. From the perspective of arteriosclerosis, apoptosis is both a mechanism which inhibits smooth muscle cell proliferation in the vascular tissue and a predominant pathway in anti-arteriosclerotic therapy.

Apoptosis, resulting from transduction of death signals triggered by a variety of endogenous stimuli, is an essential mechanism for the maintenance of homeostasis in multicellular organisms. This mechanism is activated during differentiation, in response to growth factor deprivation or to ligand-mediated engagement of specific response to genotoxic exposure. Despite the diversity of the signals triggering apoptosis, the cellular changes leading to apoptotic death are similar, suggesting that the different molecular pathways all converged into common final agonist-antagonist effector(s). However, the biochemical and genetic determinants that lead to apoptosis remain largely obscure. Sachs, L., and Lotem, J., 1993, Blood 82:15–21; Raff, M. S., 1994, Nature (Lond) 356:397–400.

Apoptosis is a cellular response to a variety of signals including ionizing radiation, UV radiation, cytokines, heat or chemotherapeutic agents. The onset of apoptosis is heralded by compaction and segregation of chromatin into sharply delineated masses that lie against the nuclear envelope, condensation of the cytoplasm, and mild convolution of the nuclear and cellular outlines. Rapid progression of the process is associated with nuclear fragmentation and marked convolution of the cellular surface with the development of pedunculated protuberances. The latter then separate to produce membrane-bound apoptotic bodies, which are phagocytosed and digested by adjacent cells. Cellular antioxidant defense mechanisms such as the reactive-oxygen scavenger enzymes, superoxide dismutase and catalase can control apoptosis. For example, there is evidence that the protooncogene Bcl-2 suppresses apoptosis through the regulation of an antioxidant pathway. (Hockenberg, D. M. et al., 1993, Cell 75: 241–251). Bcl-2 belongs to a family of related genes such as Bcl-x, Bacl, Bag, Bak and Bik with antiapoptotic function and other members such as Bax, display pro-apoptotic function (Wang, H. G. et al., 1996, Proc. Natl. Acad. Sci. USA 93: 7063). Thus, the present invention also includes a method for inducing apoptosis in cells needing to be renewed by using a combination of salts of AICA or 5-amino or substituted amino 1,2,3-triazole, or a combination of these salts with or without other agents and antioxidant therapy. Suitable antioxidants include, but are not limited to, one or more of N-acetylcysteine, vitamin E, vitamin A and its analogues, glutathione, vitamin C, cysteine, methionine and 2-mercaptoethanol.

4.2 Proliferating Cell Nuclear Antigen (PCNA)

PCNA is a highly conserved 36 kd nuclear protein associated with DNA polymerase delta. Elevated expression of PCNA occurs in the nucleus during the late $G_1$ phase immediately before onset of DNA synthesis, reaches a maximum during the S-phase and declines during the $G_2$ and M phases.

4.3. Cyclooxygenase ($COX_2$)-2 Activity

Cyclooxygenase is a rate-limiting enzyme in prostaglandin, prostacyclin and thromboxane synthesis. The protanoids-prostaglandins, prostacyclins and thromboxanes collectively known as prostanoids, play pivotal and complicated and often contradictory voles in a wide range of autocrine and paracine cellular interactions. The assumption has been that the precursor fatty acid, arachidonic acid is converted to prostanoids by the cyclooxygenase EC1.14.99.1 (COX-1) enzyme present in normal cells. A second cyclooxygenase gene, COX-2 is induced in a variety of ligands, in cells as diverse as fibroblasts, monocyctes, macrophages, smooth muscle cells, epithelial cells, endothelial cells and cancer cells. Prostanoids are thought to play a major role in the pathophysiology of rheumatoid arthritis and cancer. Karmali, R. A., et al., 1982, Prost. Leuk. Med. 8:437–446; Karmali, R. A., 1987, Eur. J. Clin. Oncol. 23:3–7. Their inflammatory activities have led to the search for a specific COX-2 inhibitor that can discriminate between COX-1 and COX-2 and an anti-inflammatory drug with substantially reduced side effects. DeWitt, D. L., Biochim. Biophys. Acta, 1991, 1083:121–134.

4.4. Target Diseases

4.4.1. Benign Breast Disease

Breast cancer is one of the most common of all human malignancies. Epidemiologic data suggest that genetic, endocrine and environmental factors may be involved in the initiation and/or the promotion of breast cancer growth. Breast cancer is one of the few tumors for which there is conclusive evidence that screening will decrease mortality. In the treatment of breast cancer, radical surgical procedures have been replaced by limited forms of surgery and medical therapies are an important component of treatment and prevention of breast cancer.

In general, a woman's risk of subsequently developing breast cancer after a biopsy that demonstrates benign disease is increased relative to the total population of women. Fibrocystic disease is the most common benign disease and is characterized by presence of macroscopic, fluid-filled cysts and a nonspecific proliferation of epithelial and mesenchymal tissue.

The increased risk of breast cancer among women with benign breast disease seems to be confined to that group of women who have histologic evidence of ductal or lobular cell proliferation on biopsy (about 30 percent of patients biopsied for benign conditions), especially those who have atypical hyperplasia (about 3 percent of biopsied patients). The relative risk for developing breast cancer in this group is 4.4 times that of an age-matched population of unselected women. In women with both atypical hyperplasia and a first-degree relative with a history of breast cancer, the risk of breast cancer is about ninefold. In such a population, an apoptosis-inducing agent would be useful in inhibiting the hyperplasia and thus eventually reducing the risk of breast cancer development. Apoptosis appears to play an important role in tissue remodeling and reaction to the environment whereby unnecessary cells may undergo cell death to allow the growth and differentiation of cells that are better geared to deal with the changing demands. Thus, agents that can selectively induce apoptotic control in precancerous or defective cells may be useful in eliminating such cells. Cancer cells circumvent the normal apoptotic mechanisms to prevent their self-destruction, which would have been indicated because of the mutations they harbor (Kerr, J. F. R. et al., 1994, Cancer 73: 2013).

4.4.2 Prostatic Hyperplasia

Development of prostatic hyperplasia is common in aging men. The prostate remains stable in size until the age of 45 and increases in frequency with age so that by 80 years of age more than 90 percent of men have prostatic hyperplasia.

The disorder is a leading cause of morbidity in elderly men. The prostate surrounds the urethra, and prostatic hyperplasia is the most common cause of obstruction to urinary outflow in men. Overall, prostatic surgery is performed in about 10 percent of men at sometime.

Prostatic hyperplasia begins in the periurethral region as a localized proliferation and progresses to compress the remaining normal gland. The hyperplastic tissue is noctular and composed of varying amounts of glandular epithelium, stroma, and smooth muscle. The hyperplasia can compress and obstruct the urethra. Urethral obstruction results from the elongation and compression of the posterior urethra. Eventually, chronic urinary retention and obstruction develop with symptoms of great discomfort.

Because the majority of men above the age 60 have some degree of prostatic hyperplasia, the presence of the disorder by itself is not an indication of treatment. However, several forms of medical or surgical treatments exist for men with more advanced symptoms. Treatment with luteinizing hormone-releasing hormone (LHRH) analogues, an inhibitor of the steroid 5α-reductase enzyme (finasteride) shrinks prostatic glandular hyperplasia. Surgery is still the benchmark treatment when symptoms include decrease in urine flow of sufficient magnitude to cause discomfort, persistent residual urine and acute urinary retention due to obstruction. Therapy with an apoptosis inducing agent that shrinks the prostatic glandular hyperplasia would therefore provide an important non-surgical medical therapy in the management and treatment of prostatic hyperplasia.

4.4.3 Prostatic Carcinoma

Prostate cancer remains the second leading cause of cancer deaths in American men and the number of patients predicted to die from prostate cancer in 1997 accounts for 14% of all cancer deaths in males. Despite increased awareness of the disease and improved methods for early detection, a large proportion of patients die of disseminated cancer that is resistant to conventional therapies. Hormonal or androgen-ablative therapy (i.e., orchiectomy, diethylstilbestrol, luteinizing-hormone releasing hormone analogues, and adrogen receptor antagonists) is the predominant systemic treatment for metastatic prostate cancer. Although an initial response to hormonal therapy is observed in 70–80% of patients with advanced disease, most tumors progress rapidly to androgen-independent growth, and only 10–20% of the patients are alive 5 years following initiating of treatment. Prostate cancer is composed of clones of androgen-dependent and androgen-independent cells even before therapy. The initial response following androgen ablation is thought to be due to the induction of apoptosis of androgen-dependent prostate cancer cells. Because adrogen-independent cells are insensitive to androgen ablation, they remain alive even in the absence of androgens. Therefore, to implement effective treatment for advanced prostate cancer, it is important to develop agents that induce apoptosis of prostate cancer cells and of the prostatic epithelium. Santen, R. J., 1992, J. Clin. Endocrinol. Metab. 75: 685–689; Isaacs, J. et al., 1992, J. Androl. 13: 457–464; Parker, S. et al., 1997, CA Cancer J. Clin. 47: 5–27.

4.4.4 Conditions Characterized by Abnormal Cell Proliferation

A number of clinical conditions are characterized by abnormal cell proliferation, e.g., psoriasis, eczema and endometriosis which result from localized spread of diseased or abnormal cells. Other conditions associated with abnormal cell proliferation include, but are not limited to, systemic lupus erythematosus, arthritis, arteriosclerosis, nerve conduction disease and cystic fibrosis. Thus, application of an apoptosis inducing agent would provide an effective modality in the management of the above conditions.

4.5. Choice of AICA Salt and Dosage

The present invention provides a number of different organic acid salts of aminoimidazole carboxamide which inhibit proliferation of defective cells and/or growth or metastasis of tumor cells, e.g., 5-aminoimidazole-4-carboxarnide orotate (AICA orotate) or 4-amino-5-imidazolecarboxamide orotate (AICA orotate) or a combination of 1,2,3,6-tetrahydro-2,6-dioxo-4-pyrimidine carboxylic acid compound with 5-amino-1H-imidazole-4-carboxamide (1:1) or a combination of orotic acid compound with 5(or 4)-aminoimidazole-4(or 5)-carboxamide (1:1); salts of AICA with aliphatic acids such as lactic, succinic, maleic, citric, and tartaric or with sugar acids such as gluconic, galactonic, etc., particularly penta and poly, hydroxycarboxylic acids to form organic acid salts; and inorganic acid salts such as hydrochlorides and/or phosphate salts of AICA suitable for use according to the methods of the present invention.

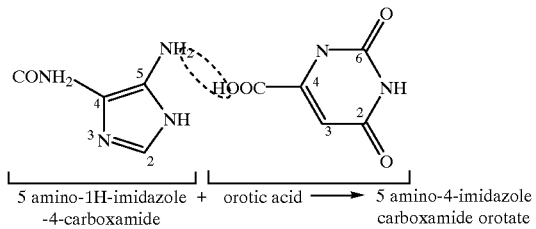

5 amino-1H-imidazole + orotic acid ⟶ 5 amino-4-imidazole
-4-carboxamide                        carboxamide orotate

4.6 Choice of Salt of 5-Amino or A Substituted Amino 1,2,3-Triazole Compound The present invention provides novel salts of 5-amino or a substituted amino 1,2,3-triazole compound which inhibit tumor cell proliferation and/or metastasis even greater than the native 5-amino or a substituted amino 1,2,3-triazole compound. The novel salts of the invention involve salts of a class of compounds of the formula:

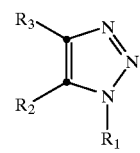

wherein, $R_1$ is

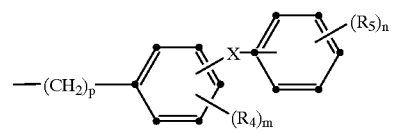

wherein p is 0 to 2; m is 0 to 4; and n is 0 to 5; X is O, S, SO, $SO_2$, CO, CHCN, $CH_2$ or $C=NR_6$ where $R_6$ is hydrogen, loweralkyl, hydroxy, loweralkoxy, amino, loweralkylamino, diloweralkylamino or cyano; and, $R_4$ and $R_5$ are independently halogen, cyano, trifluoromethyl, loweralkanoyl, nitro, loweralkyl, loweralkoxy, carboxy, lowercarbalkoxy, trifuloromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl; $R_2$ is amino, mono or diloweralkyl amino, acetamido, acetimido, ureido, formamido, formamido or guanidino; and $R_3$ is carbamoyl, cyano, carbazoyl, amidino or N-hydroxycarbamoyl; wherein the loweralkyl, loweralkyl containing, loweralkoxy and loweralkanoyl groups contain from 1 to 3 carbon atoms.

In particular, the composition of the present invention includes, but is not limited to a salt of L651582 or 5-amino-1-(4-[4-chlorobenzoyl]-3,5-dichlorobenzyl)-1,2,3-triazole-4-carboxamide. Accordingly, an effective dose of a salt of 5-amino or a substituted amino 1,2,3-triazole compound is administered to an individual in need thereof.

The 5-amino or a substituted amino 1,2,3-triazole compound is reacted with orotic acid, aliphatic acids including, but not limited to lactic, succinic, maleic, citric and tartaric, or with sugar acids including, but not limited to, gluconic and galactonic, particularly penta and poly hydroxycarboxylic acids, to form organic salts; and inorganic acids including, but not limited to, hydrochloric and phosphonic acid to form salts of 5 amino or a substituted amino 1,2,3-triazole compound suitable for use according to the methods of the present invention.

4.7 Dosage and Formulation

AICA salts or salts of 5-amino or substituted amino 1,2,3-triazoles may be formulated into pharmaceutical preparations for administration to mammals for treatment of primary and metastatic neoplasms and other cell proliferative diseases.

Many of the AICA or triazole salt compounds may be provided as organic acid salts with pharmaceutically compatible counterions, a form in which they are merely water-soluble. Pharmaceutically compatible salts may be formed with many acids, including, but not limited to, aliphatic acids such as lactic, succinic, maleic, citric and tartaric or with sugar acids such as gluconic, galactonic, etc., particularly penta and poly, hydroxycarboxylic acids and inorganic acids including, but not limited to hydrochloric and phosphoric acid. Salts tend to be more soluble in aqueous or other protonic solvents that are the corresponding free base forms.

The therapeutic compounds or pharmaceutical compositions may be administered intravenously, intraperitoneally, subcutaneously, intramuscularly, intrathecally, orally, rectally, topically, or by aerosol.

Formulations suitable for oral administration include liquid solutions of the active compound dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations may be in unit dose or multi-dose sealed containers.

5. EXAMPLE: AICA and TRIAZOLE EFFECTS ON RAT PROSTATE AND MAMMARY CANCER CELLS The effect of AICA Salts (Orazamide HCL and Orazamide Orotate), triazole (L651582) and triazole salt (L6511582 orotate) were studied in vitro in a) the rat mammary cell line established from nitrosomethyl urea (MNU)-induced tumor, and b) the AT-1 androgen independent rat prostatic cancer cell line.

5.1 Cell Cultures

The rat mammary cell line (obtained from the American Health Foundation, Valhalla, N.Y.) were grown in Dulbecco's Modified Eagle Medium (DMEM with 10%) fetal calf serum (Hyclone, Inc.) and 0.1% dexamethasone (DMSO) (Sigma Chemical Corp., St. Louis, Mo.). The cells were maintained in T-75 plastic flasks and were detached by trypsinization, counted and diluted in DMEM to provide 30,000 cells/ml. The cells were then plated on 60×15 mm tissue culture dishes using 2 m/dish to provide 60,000 cells/dish. Cultures were grown in a 37° C. water-saturated incubator in an atmosphere of 5% carbordioxide and 95% air. Cells were counted after 7 days by detaching the cells using phosphate buffer saline (PBS) without $Ca^{+2}$ and $Mg^{2+}$ and a solution containing 0.05% trypsin and 0.02% EDTA. Cells were brought up to a volume of 5 ml with DMEM and counted in an electronic particle counter (Coulter Model ZB1). Some cells were plated on slide chambers which were subsequently used to study cell proliferation by measuring PCNA.

The AT-1 androgen independent prostatic cancer cells were obtained from the Prostate and Breast Laboratories of the Johns Hopkins Oncology Center. The cells were grown in RPMI 1640 medium (Grand island Biologicals) with L-glutamine and 10% fetal calf serum (Hyclone Inc.) and 0.1% dexamethasone (Sigma Chemical Corp.). The cells were maintained in T-75 flasks at 37° C. in a water-saturated incubator in an atmosphere if 5% carbon dioxide and 95% air. The cells (60,000 cell/dish) were grown for 7 days, counted and plated on slide chambers for carrying out cell proliferation studies by measuring PCNA.

The following test reagents were dissolved in DMSO and added at concentrations ranging from $10^{-7}M$ to $5\times10^{-6}$: orazamide orotate, orazamide orotate hydrochloride, L651582 and L651582 orotate. For each concentration triplicate cultures were prepared.

The results of varying concentrations of test agents cell number in the two cell lines are shown in TABLE 1 to TABLE 8.

Orazamide orotate had no significant inhibitory effects on proliferation of MNU cells.

TABLE 1

Cell Line: MNU-Tumor Cells
Drug: Orazamide Orotate

| GROUP:DOSE | 0 | DAYS AFTER DRUG ADDITION | | |
|---|---|---|---|---|
| | | 1 | 4 | 6 |
| CONTROL | $1.98 \times 10^{5(a)}$ | $3.99 \times 10^5$ | $1.5 \times 10^6$ | $3.30 \times 10^6$ |
| Vehicle (DMSO) | | $4.70 \times 10^5$ | | |
| $5 \times 10^{-6}$ | | $3.8 \times 10^5$ | $1.7 \times 10^6$ | $3.0 \times 10^6$ |
| $1 \times 10^{-6}$ | | $3.5 \times 10^5$ | $0.6 \times 10^6$ | $2.7 \times 10^6$ |
| $0.5 \times 10^{-6}$ | | $4.9 \times 10^5$ | $0.46 \times 10^6$ | $2.5 \times 10^6$ |
| $0.1 \times 10^{-6}$ | | $4.9 \times 10^5$ | $0.78 \times 10^6$ | $2.5 \times 10^6$ |
| $0.05 \times 10^{-6}$ | | $3.4 \times 10^5$ | $0.6 \times 10^6$ | $2.8 \times 10^6$ |

Orazamide HCl inhibited the proliferation of MNU cells on day 1 but by days 4 and 6 there was no difference between MNU treated cells and control MNU cells.

TABLE 2

Cell Line: MNU-Tumor Cells
Drug: Orazamide-HCL

| GROUP:DOSE | DAYS AFTER DRUG ADDITION | | | |
|---|---|---|---|---|
| | 0 | 1 | 4 | 6 |
| CONTROL | $1.98 \times 10^{5(a)}$ | $3.99 \times 10^5$ | $1.5 \times 10^6$ | $3.3 \times 10^6$ |
| Vehicle (DMSO) | | $4.70 \times 10^5$ | | |
| $5 \times 10^{-6}$ | | $3.84 \times 10^5$ | $2.5 \times 10^6$ | $4.1 \times 10^6$ |
| $1 \times 10^{-6}$ | | $2.72 \times 10^5$ | $2.8 \times 10^6$ | $3.8 \times 10^6$ |
| $0.5 \times 10^{-6}$ | | $1.71 \times 10^5$ | $2.4 \times 10^6$ | $3.4 \times 10^6$ |
| $0.1 \times 10^{-16}$ | | $2.43 \times 10^5$ | $3.4 \times 10^6$ | $3.4 \times 10^6$ |
| $0.05 \times 10^{-6}$ | | $2.60 \times 10^5$ | $2.4 \times 10^6$ | $3.3 \times 10^6$ |

In marked contrast, application compound L651582 resulted in marked suppression of cell proliferation in MNU cells at the concentration of 5 µg/ml.

TABLE 3

Cell Line: Rat Mammary Cancer Cells
Drug: Compound L651582

| GROUP:DOSE | DAYS AFTER DRUG ADDITION | | |
|---|---|---|---|
| | 0 | 5 | 7 |
| CONTROL | $2.93 \times 10^{5(a)}$ | $9.5 \times 10^5$ | $1.3 \times 10^6$ |
| Vehicle (DMSO) | | $8.3 \times 10^5$ | $1.2 \times 10^6$ |
| $5 \times 10^{-6}$ | | $0.6 \times 10^5$ | $.08 \times 10^6$ |
| $1 \times 10^{-6}$ | | $5.9 \times 10^5$ | $1.0 \times 10^6$ |
| $0.5 \times 10^{-6}$ | | $9.7 \times 10^5$ | $1.5 \times 10^6$ |
| $0.1 \times 10^{-6}$ | | $9.1 \times 10^5$ | $1.8 \times 10^6$ |
| $0.05 \times 10^{-6}$ | | $8.4 \times 10^5$ | $1.6 \times 10^6$ |

Similarly, application of L651582 orotate suppressed cell proliferation in MNU cells at 5 µg/ml.

TABLE 4

Cell Line: Rat Mammary Cancer Cells
Drug: Compound L651582 - Orotate

| GROUP:DOSE | DAYS AFTER DRUG ADDITION | | |
|---|---|---|---|
| | 0 | 5 | 7 |
| CONTROL | $2.93 \times 10^{5(a)}$ | $9.5 \times 10^5$ | $1.3 \times 10^6$ |
| Vehicle (DMSO) | | $8.3 \times 10^5$ | $1.2 \times 10^6$ |
| $5 \times 10^{-6}$ | | $0.57 \times 10^5$ | $0.53 \times 10^5$ |
| $1 \times 10^{-6}$ | | $7.6 \times 10^5$ | $1.0 \times 10^6$ |
| $0.5 \times 10^{-6}$ | | $8.4 \times 10^5$ | $1.7 \times 10^6$ |
| $0.1 \times 10^{-6}$ | | $10.6 \times 10^5$ | $1.9 \times 10^6$ |
| $0.05 \times 10^{-6}$ | | $9.3 \times 10^5$ | $2.0 \times 10^6$ |

Neither orazamide orotate nor orazamide hydrochloride had any effect on proliferation of AT-1 prostate cancer cells (Table 5 and Table 6)

TABLE 5

Cell Line: AT-1 Androgen independent Rat Prostate Cancer Cells
Drug: Orazamide - Orotate

| GROUP:DOSE | DAYS AFTER DRUG ADDITION | | |
|---|---|---|---|
| | 0 | 3 | 7 |
| CONTROL | $1.13 \times 10^{5(a)}$ | $1.71 \times 10^5$ | $5.71 \times 10^5$ |
| Vehicle (DMSO) | | $2.30 \times 10^5$ | $6.10 \times 10^5$ |
| $5 \times 10^{-6}$ | | $1.68 \times 10^5$ | $5.05 \times 10^5$ |
| $1 \times 10^{-6}$ | | $1.71 \times 10^5$ | $9.47 \times 10^5$ |

TABLE 5-continued

Cell Line: AT-1 Androgen independent Rat Prostate Cancer Cells
Drug: Orazamide - Orotate

| GROUP:DOSE | DAYS AFTER DRUG ADDITION | | |
|---|---|---|---|
| | 0 | 3 | 7 |
| $0.5 \times 10^{-6}$ | | $2.20 \times 10^5$ | $9.63 \times 10^5$ |
| $0.1 \times 10^{-6}$ | | $2.31 \times 10^5$ | $7.57 \times 10^5$ |
| $0.05 \times 10^{-6}$ | | $2.84 \times 10^5$ | $8.49 \times 10^5$ |

TABLE 6

Cell Line: AT-1 Androgen Independent Rat prostate Cancer Cells
Drug: Orazamide - HCL

| GROUP:DOSE | DAYS AFTER DRUG ADDITION | | |
|---|---|---|---|
| | 0 | 3 | 7 |
| CONTROL | $1.13 \times 10^{5(a)}$ | $1.71 \times 10^5$ | $5.71 \times 10^5$ |
| Vehicle (DMSO) | | $2.30 \times 10^5$ | $6.10 \times 10^5$ |
| $5 \times 10^{-16}$ | | $1.57 \times 10^5$ | $5.33 \times 10^5$ |
| $1 \times 10^{-6}$ | | $2.61 \times 10^5$ | $7.30 \times 10^5$ |
| $0.5 \times 10^{-6}$ | | $3.37 \times 10^5$ | $7.58 \times 10^5$ |
| $0.1 \times 10^{-6}$ | | $2.75 \times 10^5$ | $6.27 \times 10^5$ |
| $0.05 \times 10^{-6}$ | | $3.17 \times 10^5$ | $6.45 \times 10^5$ |

However, both L651582 and L651582 orotate inhibited proliferation of AT-1 cells in a dose dependent manner, with maximum inhibition occurring at 5 µg/ml (Table 7 and Table 8 respectively)

TABLE 7

Cell Line: AT-1 Androgen independent Cancer Cells
Drug: Compound L651582

| GROUP:DOSE | DAYS AFTER DRUG ADDITION | | |
|---|---|---|---|
| | 0 | 4 | 7 |
| CONTROL | $1.8 \times 10^{5(a)}$ | $1.2 \times 10^6$ | $2.4 \times 10^6$ |
| Vehicle (DMSO) | | $1.2 \times 10^6$ | $2.4 \times 10^6$ |
| $5 \times 10^{-6}$ | | $0.3 \times 10^6$ | $0.3 \times 10^5$ |
| $1 \times 10^{-6}$ | | $0.6 \times 10^6$ | $1.1 \times 10^6$ |
| $0.5 \times 10^{-6}$ | | $0.79 \times 10^6$ | $1.6 \times 10^6$ |
| $0.1 \times 10^{-6}$ | | $1.2 \times 10^6$ | $2.4 \times 10^6$ |
| $0.05 \times 10^{-6}$ | | $1.1 \times 10^6$ | $2.4 \times 10^6$ |

TABLE 8

Cell Line: AT-1 Androgen Independent Cancer Cells
Drug: Compound L651582 - Orotate

| GROUP:DOSE | DAYS AFTER DRUG ADDITION | | |
|---|---|---|---|
| | 0 | 4 | 7 |
| CONTROL | $1.8 \times 10^{5(a)}$ | $1.2 \times 10^6$ | $2.4 \times 10^6$ |
| Vehicle (DMSO) | | $1.2 \times 10^6$ | $2.4 \times 10^6$ |
| $5 \times 10^{-6}$ | | $0.29 \times 10^6$ | $0.36 \times 10^6$ |
| $1 \times 10^{-6}$ | | $0.6 \times 10^6$ | $0.67 \times 10^6$ |
| $0.5 \times 10^{-6}$ | | $0.8 \times 10^6$ | $1.4 \times 10^6$ |
| $0.1 \times 10^{-6}$ | | $0.97 \times 10^6$ | $1.6 \times 10^6$ |
| $0.05 \times 10^{-6}$ | | $1.0 \times 10^6$ | $2.4 \times 10^6$ |

5.2 Histochemistry (a) Proliferating Cell Nuclear Antigen (PCNA)

PCNA is a highly conserved 36 kd nuclear protein associated with DNA polymerase delta. Elevated expression of PCNA occurs in the nucleus during the late $G_1$ phase immediately before onset of DNA synthesis, reaches a maximum during the S-phase and declines during the $G_2$ and M phases. Antigenic sites appear as light to dark brown-red colors with antibody (clone PC10) obtained from Zymed Labs (San Francisco, Calif.).

In the MNU cells, there was no significant difference in PCNA staining cells in the orazamide orotate, orazamide HCl, L651582 or L651582 orotate-treated cells in comparison with the untreated MNU cells.

In the AT-1 prostate cancer cells, the PCNA results paralleled the cell count results, i.e., PCNA staining was seen in about 25 percent of the cells treated with L651582 (FIG. 1) or L651582 orotate (FIG. 2) (each at 5 µg/ml). In contrast, cells treated with orazamide orotate or orazamide HCl had no change in PCNA staining in comparison with the untreated controls (FIG. 3).

These results indicate a close concordance of molecular events associated with DNA synthesis and cell proliferation and demonstrate an inhibitory effect of L651582 and L651582 orotate in the AT-1 prostate cancer cells.

(b) Klenow Assay

Programmed cell death or apoptosis is a selective process of physiological cell deletion. The key features are nuclear chromatin condensation and compactness of cell organelles. Apoptosis is associated with endogenous endonuclease activity leading to chromatin (DNA) cleavage. The method of detection involves reacting terminal deoxynucleotide transferase (Tdt) and deoxynucleotides with free 3'-OH ends of DNA. Tdt is used to incorporate biotinylated deoxyuridine at sites of DNA breaks. The signal is then amplified by visualizing with streptavidin-peroxidase staining. Diaminobenzidine (DAB) is then allowed to react with the labeled sample to generate an insoluble colored substrate at the site of DNA fragmentation. A dark brown DAB signal indicates positive staining while shades of blue-green signify a non-reactive cell. The Frag. EL-Klenow DNA fragmentation kit, obtained from Oncogene Research Products (Cambridge, Mass.) was used to detect cleaved DNA in this study.

In the MNU cells, orazamide orotate or orazamide HCL treatment had very little effect on Klenow staining. However, L651582 or L651582 orotate treatment resulted in greater Klenow staining in comparison with the control (FIG. 4 to FIG. 6).

In the AT-1 prostate cancer cells, both orazamide orotate and orazamide HCl induced apoptotic changes in that intensely staining hot spots were seen in the orazamide treated groups. Similarly, L651582 and L651582 orotate induced apoptotic changes in the treated cells compared with the untreated cells (FIG. 7 to FIG. 11).

These results indicate that both orazamide salts and L651582 or L651582 orotate induce apoptotic changes in AT-1 cells as measured by the Klenow assay.

(c) Bcl-2 Gene

Bcl-2 belongs to a family of genes unique among proto-oncogenes because rather than promoting cell proliferation, Bcl-2 fosters cell survival. Constitutive activation of Bcl-2 contributes to the etiology of human follicular lymphomas and over-expression of Bcl-2 inhibits multiple forms of apoptosis (Korsmeyer, S. J., 1992, Blood 80: 879–886 and Sentman, C. L. et al., 1991, Cell 67: 879–888). Bcl-2 is located in the mitochondrial membrane, the endoplasmic reticulum and the nuclear envelope. Bcl-2 activity was measured using antibody against Bcl-2 obtained from Zymed Laboratories, San Franscico, Calif.

In the MNU cells, the control untreated cells showed marked intense staining patterns indicating more Bcl-2 than in the treated cells which had been exposed to orazamide orotate, orazamide HCl, L651582 or L651582 orotate (FIG. 12 to FIG. 16). These results indicate that the compositions tested in these studies induced apoptotic changes in part by inhibiting the activity of Bcl-2.

6. EXAMPLE: EFFECT OF ORAZAMIDE OROTATE AND L651582 OROTATE ON COX-2 ACTIVITY IN VITRO

One unit of COX-1/COX-2 enzyme (Cayman Chemical Company, Ann Arbor, Mich.) is suspended in 0.5 ml of pH 8.0 Tris-HCL buffer (100 mM) containing hematin (1 mM) and phenol (2 mM), as co-factors. The reaction medium is preincubated with the drug for 2 minutes at 37° C., then 100 mM of arachidonic acid is added and incubated for 2 minutes at 37° C. (Sigma, St. Louis, Mo.) To terminate the reaction and extract $PGE_2$, 2 ml of h-hexane/ethyl acetate (2:1, v/v) is added to the reaction mixture, centrifuged and the aqueous phase is separated (by freezing) from the organic reside. $PGE_2$ is measured by radioimmuno orotate assay (Karmali, R. A. et al., 1982, Prost. Med. 8:565–577).

Both orazamide orotate and L651582 orotate inhibit COX-2 enzyme activity in a concentration dependent manner, whereas they have no effect on COX-1 activity. FIG. 17, Indomethacin inhibits both COX-1 and COX-2 activity at $10 \times 10^{-7}$M. Thus, both orazamide orotate and L651582 orotate have a selective inhibition against COX-2 activity. FIG. 18.

The present invention is not to be limited in scope by the embodiments disclosed in the examples which are intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall there between.

What is claimed is:

1. A method of inducing apoptosis in an animal, comprising identifying an animal having cells suspected of needing said apoptosis and administering to said animal an apoptosis-inducing amount of a composition comprising a salt of 5-aminoimidazole-4-carboxamide.

2. The method of claim 1, wherein said animal is a human.

3. The method according to claim 1, wherein the composition comprises an organic salt derived from a combination of 5-aminoimidazole-4-carboxamide and an acid selected from the group consisting of orotic, lactic, succinic, maleic, citric, tartaric, gluconic and galactonic.

4. The method according to claim 1, wherein the composition comprises an inorganic acid salt derived from a combination of 5-aminoimidazole-4-carboxamide and an acid selected from the group consisting of hydrochloric and phosphoric.

5. The method according to claim 1, wherein the composition comprises 5-aminoimidazole-4-carboxamide orotate.

6. The method according to claim 1, wherein said cells in need of apoptosis are selected from the group consisting of preneoplastic cells, transformed cells, aging cells, cancerous cells, preinflammatory cells, inflammatory cells and arteriosclerotic cells.

7. The method according to claim 1, wherein the composition is administered orally, intravenously, transcutaneously or trandermally.

8. A method of inhibiting cell proliferation in an animal, comprising identifying an animal having cells suspected of needing such inhibition and administering to said animal cell proliferation-inhibiting amount of a composition comprising a salt of 5-aminoimidazole-4-carboxamide.

9. The method of claim 8, wherein said animal is a human.

10. The method according to claim 8, wherein the composition comprises an organic salt derived from a combination of 5-aminoimidazole-4-carboxamide and an acid selected from the group consisting of orotic, lactic, succinic, maleic, citric, tartaric, gluconic and galactonic.

11. The method according to claim 8, wherein the composition comprises an inorganic acid salt derived from a combination of 5-aminoimidazole-4-carboxamide and an acid selected from the group consisting of hydrochloric and phosphoric.

12. The method according to claim 8, wherein the composition comprises 5-aminoimidazole-4-carboxamide orotate.

13. The method according to claim 8, wherein said cells in need of apoptosis are selected from the group consisting of preneoplastic cells, transformed cells, aging cells, cancerous cells, preinflammatory cells, inflammatory cells and arteriosclerotic cells.

14. The method according to claim 8, wherein the composition is administered orally, intravenously, transcutaneously or transdermally.

15. A method of inhibiting cyclooxygenase activity in an animal, comprising identifying an animal having cells suspected of needing such inhibition and administering to said animal a cycloxygenase inhibiting amount of a composition comprising a salt of 5-aminoimidazole-4-carboxamide.

16. The method according to claim 15, wherein said animal is a human.

17. The method according to claim 15, wherein the composition comprises an organic salt derived from a combination of 5-aminoimidazole-4-carboxamide and an acid selected from the group consisting of orotic, lactic, succinic, maleic, citric, tartaric, gluconic and galactonic.

18. The method according to claim 15, wherein the composition comprises an inorganic acid salt derived from a combination of 5-aminoimidazole-4-carboxamide and an acid selected from the group consisting of hydrochloric and phosphoric.

19. The method according to claim 15, wherein the composition comprises 5-aminoimidazole-4-carboxamide orotate.

20. The method according to claim 15, wherein said cells in need of apoptosis are selected from the group consisting of preneoplastic cells, aging cells, cancerous cells, preinflammatory cells, inflammatory cells and arteriosclerotic cells.

21. The method according to claim 15, wherein the composition is administered orally, intravenously, transcutaneously or transdermally.

22. A method of inducing apoptosis in an animal, comprising identifying an animal having cells suspected of needing said apoptosis and administering to said animal an apoptosis-inducing amount of a composition comprising a salt of 5-amino-1-(4-[4-chlorobenzoyl]-3,5-dichlorobenzyl)-1,2,3-triazole-4-carboxamide.

23. The method of claim 22, wherein said animal is a human.

24. The method according to claim 22 wherein the composition comprises an organic salt derived from a combination of 5-amino-1-(4-[4-chlorobenzoyl]-3,5-dichlorobenzyl)-1,2,3-triazole-4-carboxamide and an acid selected from the group consisting of orotic, lactic, succinic, maleic, citric, tartaric, gluconic and galactonic.

25. The method according to claim 22, wherein the composition comprises an inorganic acid salt derived from a combination of 5-amino-1-(4-[4-chlorobenzoyl]- 3,5-dichlorobenzyl)-1,2,3-triazole-4-carboxamide and an acid selected from the group consisting of hydrochloric and phosphoric.

26. The method according to claim 22, wherein the composition comprises 5-amino-1-(4-[4-chlorobenzoyl]-3,5-dichlorobenzyl)-1,2,3-triazole-4-carboxamide.

27. The method according to claim 22, wherein said cells in need of apoptosis are selected from the group consisting of preneoplastic cells, transformed cells, aging cells, cancerous cells, preinflammatory cells, inflammatory cells and arteriosclerotic cells.

28. The method according to claim 22, wherein the composition is administered orally, intravenously, transcutaneously or trandermally.

29. A method of inhibiting cell proliferation in an animal, comprising identifying an animal having cells suspected of needing such inhibition and administering to said animal cell proliferation-inhibiting amount of a composition comprising a salt of 5-amino-1-(4-[4-chlorobenzoyl]-3,5-dichlorobenzyl)-1,2,3-triazole-4-carboxamide.

30. The method of claim 29, wherein said animal is a human.

31. The method according to claim 29, wherein the composition comprises an organic salt derived from a combination of 5-amino-1-(4-[4-chlorobenzoyl]-3,5-dichlorobenzyl)-1,2,3-triazole-4-carboxamide and an acid selected from the group consisting of orotic, lactic, succinic, maleic, citric, tartaric, gluconic and galactonic.

32. The method according to claim 29, wherein the composition comprises an inorganic acid salt derived from a combination of 5-amino-1-(4-[4-chlorobenzoyl]-3,5-dichlorobenzyl)-1,2,3-triazole-4-carboxamide and an acid selected from the group consisting of hydrochloric and phosphoric.

33. The method according to claim 29, wherein the composition comprises 5-amino-1-(4-[4-chlorobenzoyl]-3,5-dichlorobenzyl)-1,2,3-triazole-4-carboxamide.

34. The method according to claim 29, wherein said cells in need of apoptosis are selected from the group consisting of preneoplastic cells, transformed cells, aging cells, cancerous cells, preinflammatory cells, inflammatory cells and arteriosclerotic cells.

35. The method according to claim 29, wherein the composition is administered orally, intravenously, transcutaneously or transdermally.

36. A method of inhibiting cyclooxygenase activity in an animal, comprising identifying an animal having cells suspected of needing such inhibition and administering to said animal a cycloxygenase inhibiting amount on a composition comprising a salt of 5-amino-1-(4-[4-chlorobenzoyl]-3,5-dichlorobenzyl)-1,2,3-triazole-4-carboxamide.

37. The method according to claim 36, wherein said animal is a human.

38. The method according to claim 36, wherein the composition comprises an organic salt derived from a combination of 5-amino-1-(4-[4-chlorobenzoyl]-3,5-dichlorobenzyl)-1,2,3-triazole-4-carboxamide and an acid selected from the group consisting of orotic, lactic, succinic, maleic, citric, tartaric, gluconic and galactonic.

39. The method according to claim 36, wherein the composition comprises an inorganic acid salt derived from a combination of 5-amino-1-(4-[4-chlorobenzoyl]-3,5-dichlorobenzyl)-1,2,3-triazole-4-carboxamide and an acid selected from the group consisting of hydrochloric and phosphoric.

40. The method according to claim 36, wherein the composition comprises 5-amino-1-(4-[4-chlorobenzoyl]-3,5-dichlorobenzyl)-1,2,3-triazole-4-carboxamide.

41. The method according to claim 36, wherein said cells in need of apoptosis are selected from the group consisting of preneoplastic cells, aging cells, cancerous cells, preinflammatory cells, inflammatory cells and arteriosclerotic cells.

42. The method according to claim 36, wherein the composition is administered orally, intravenously, transcutaneously or transdermally.

43. The method according to claim 8, wherein the composition further comprises 5-amino-1-(4-[4-chlorobenzoyl]-3,5-dichlorobenzyl)-1,2,3-triazole-carboxamide orotate.

44. The method according to claim 8, wherein a method of inhibiting cell proliferation in an animal, further comprising identifying an animal having cells suspected of needing such inhibition and administering to said animal cell proliferation-inhibiting amount of a composition comprising a salt of 5-amino-1-(4-[4-chlorobenzoyl]-3,5-dichlorobenzyl)-1,2,3-triazole-4-carboxamide.

45. A method according to claim 15, wherein a method of inhibiting cyclooxygenase activity in an animal, further comprising identifying an animal having cells suspected of needing such inhibition and administering to said animal a cycloxygenase inhibiting amount on a composition comprising a salt of 5-amino-1-(4-[4-chlorobenzoyl]-3,5-dichlorobenzyl)-1,2,3-triazole-4-carboxamide.

46. The method of claim 1 further comprising antioxidant therapy selected from the group consisting of N-acetycysteine, vitamin E, vitamin A and its analogues, glutathione, vitamin C, cysteine, methionine and 2-mercaptoethanol.

47. The method of claim 8 further comprising antioxidant therapy selected from the group consisting of N-acetycysteine, vitamin E, vitamin A and its analogues, glutathione, vitamin C, cysteine, methionine and 2-mercaptoethanol.

48. The method of claim 15 further comprising antioxidant therapy selected from the group consisting of N-acetycysteine, vitamin E, vitamin A and its analogues, glutathione, vitamin C, cysteine, methionine and 2-mercaptoethanol.

49. The method of claim 22 further comprising antioxidant therapy selected from the group consisting of N-acetycysteine, vitamin E, vitamin A and its analogues, glutathione, vitamin C, cysteine, methionine and 2-mercaptoethanol.

50. The method of claim 29 further comprising antioxidant therapy selected from the group consisting of N-acetycysteine, vitamin E, vitamin A and its analogues, glutathione, vitamin C, cysteine, methionine and 2-mercaptoethanol.

51. The method of claim 36 further comprising antioxidant therapy selected from the group consisting of N-acetycysteine, vitamin E, vitamin A and its analogues, glutathione, vitamin C, cysteine, methionine and 2-mercaptoethanol.

* * * * *